(12) United States Patent
Koyrakh et al.

(10) Patent No.: US 9,934,617 B2
(45) Date of Patent: Apr. 3, 2018

(54) SYSTEMS AND METHODS FOR VISUALIZING AND ANALYZING CARDIAC ARRHYTHMIAS USING 2-D PLANAR PROJECTION AND PARTIALLY UNFOLDED SURFACE MAPPING PROCESSES

(71) Applicant: St. Jude Medical, Atrial Fibrillation Division, Inc., St. Paul, MN (US)

(72) Inventors: Lev A. Koyrakh, Plymouth, MN (US); Eric J. Voth, Maplewood, MN (US)

(73) Assignee: ST. JUDE MEDICAL, ATRIAL FIBRILLATION DIVISION, INC., St. Paul, MN (US)

(*) Notice: Subject to any disclaimer, the term of this patent is extended or adjusted under 35 U.S.C. 154(b) by 130 days.

(21) Appl. No.: 14/780,611

(22) PCT Filed: Apr. 17, 2014

(86) PCT No.: PCT/US2014/034467
§ 371 (c)(1),
(2) Date: Sep. 28, 2015

(87) PCT Pub. No.: WO2014/172524
PCT Pub. Date: Oct. 23, 2014

(65) Prior Publication Data
US 2016/0055681 A1  Feb. 25, 2016

Related U.S. Application Data

(60) Provisional application No. 61/813,429, filed on Apr. 18, 2013.

(51) Int. Cl.
*G06T 17/00* (2006.01)
*G06T 19/20* (2011.01)
(Continued)

(52) U.S. Cl.
CPC ............ *G06T 19/20* (2013.01); *A61B 5/0408* (2013.01); *A61B 5/0422* (2013.01); *G06T 11/00* (2013.01);
(Continued)

(58) Field of Classification Search
CPC .......... G06T 7/60; G06T 7/0012; G06T 15/08
See application file for complete search history.

(56) References Cited

U.S. PATENT DOCUMENTS

| 6,285,372 B1 * | 9/2001 | Cowsar | G06T 17/20 345/420 |
| 2005/0093861 A1 * | 5/2005 | Moreau-Gobard | G06T 15/08 345/419 |

(Continued)

FOREIGN PATENT DOCUMENTS

| JP | 2004326245 | 11/2004 |
| WO | 2007/137045 | 11/2007 |

OTHER PUBLICATIONS

Termeer, Maurice et al.; "CoViCAD: Comprehensive Visualization of Coronary Artery Disease", IEEE Transactions on Visualization and Computer Graphics, vol. 13, No. 6, Nov./Dec. 2007.

*Primary Examiner* — Phi Hoang
(74) *Attorney, Agent, or Firm* — Dykema Gossett PLLC

(57) ABSTRACT

A method for projecting a 3D surface geometry onto a planar projection comprises: obtaining a 3D geometry of a chamber surface using an algorithm that generates angles and distances between points on the chamber surface that represent mapping information; applying a cutting curve to at least two points on the chamber surface; and at least partially unfolding at least a portion of the chamber surface along the cutting curve to form a planar projection that optimally preserves the angles and distances between points on the chamber surface.

30 Claims, 9 Drawing Sheets

(51) Int. Cl.
*A61B 5/042* (2006.01)
*G06T 19/00* (2011.01)
*A61B 5/0408* (2006.01)
*G06T 11/00* (2006.01)
*G06T 17/20* (2006.01)

(52) U.S. Cl.
CPC ............ *G06T 17/205* (2013.01); *G06T 19/00* (2013.01); *G06T 2210/41* (2013.01); *G06T 2219/008* (2013.01); *G06T 2219/2004* (2013.01); *G06T 2219/2008* (2013.01)

(56) References Cited

U.S. PATENT DOCUMENTS

| | | | | |
|---|---|---|---|---|
| 2005/0099416 | A1* | 5/2005 | Moreau-Gobard | G06T 7/0012 345/419 |
| 2005/0156594 | A1* | 7/2005 | Lorenz | G01R 33/3415 324/309 |
| 2005/0209525 | A1* | 9/2005 | Bojovic | A61B 5/04011 600/512 |
| 2006/0235294 | A1* | 10/2006 | Florin | A61B 5/05 600/425 |
| 2006/0251307 | A1 | 11/2006 | Florin et al. | |
| 2009/0022387 | A1 | 1/2009 | Shirahata et al. | |
| 2009/0153577 | A1* | 6/2009 | Ghyme | G06T 15/04 345/582 |
| 2009/0214097 | A1* | 8/2009 | Mohamed | G06T 7/0012 382/131 |
| 2010/0195878 | A1* | 8/2010 | Vion | G06T 19/00 382/128 |
| 2010/0201687 | A1* | 8/2010 | Breeuwer | G06T 15/08 345/424 |
| 2011/0065506 | A1* | 3/2011 | Sugden | G06T 15/04 463/32 |
| 2011/0304332 | A1* | 12/2011 | Mahfouz | A61F 2/3094 324/309 |
| 2014/0301179 | A1* | 10/2014 | Rich | G06T 9/00 369/275.4 |

* cited by examiner

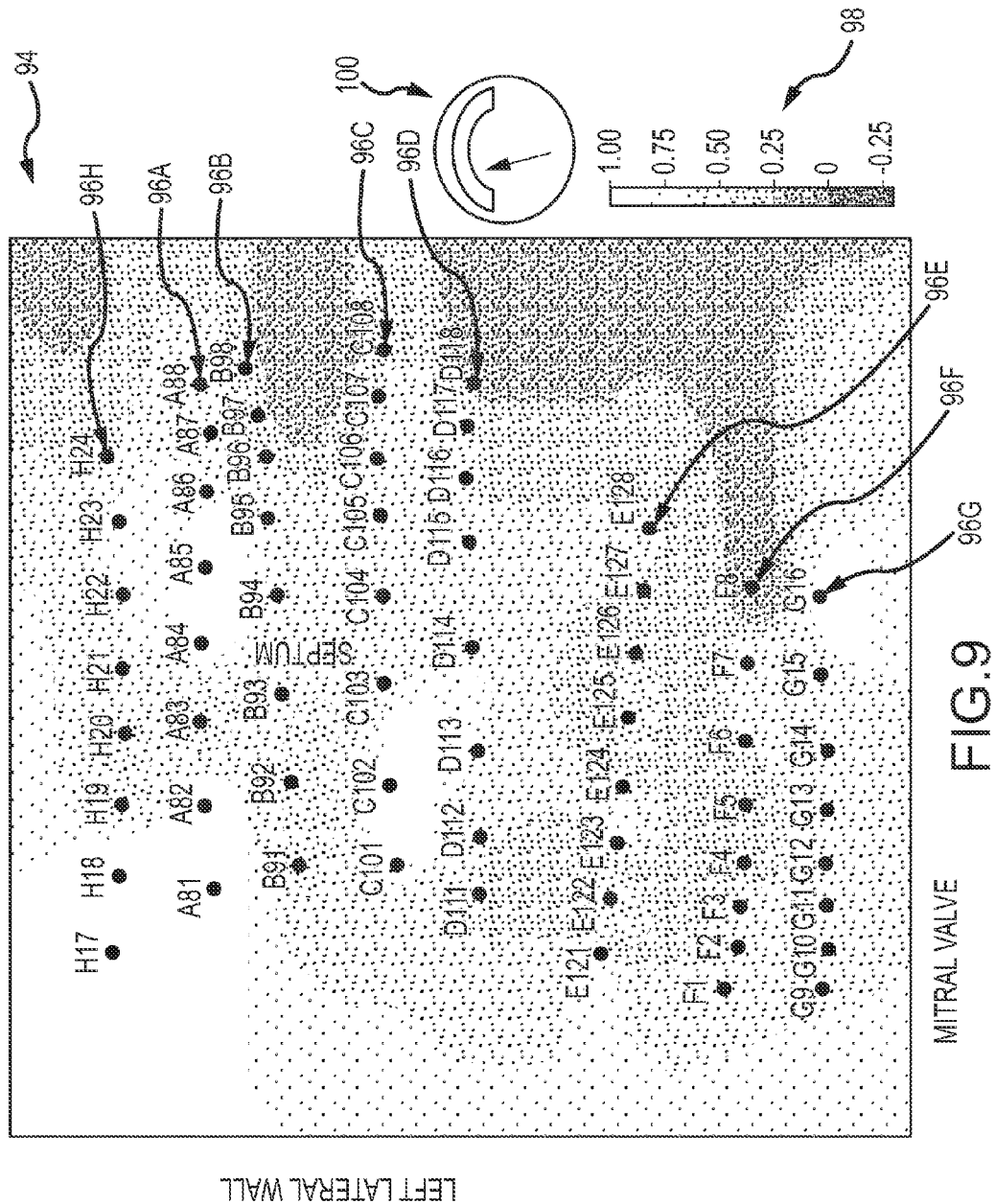

SYSTEMS AND METHODS FOR VISUALIZING AND ANALYZING CARDIAC ARRHYTHMIAS USING 2-D PLANAR PROJECTION AND PARTIALLY UNFOLDED SURFACE MAPPING PROCESSES

BACKGROUND a. Field of the Invention

The present disclosure relates generally to image generation in medical device mapping systems. More particularly, the present disclosure relates to generation of two-dimensional images from three-dimensional models.

b. Background Art

Current intracardiac navigational and mapping systems use a three-dimensional (3D) data representation in which a 3D geometric model of the endocardium is drawn on a computer display. Typical systems involve the use of one or more catheters to simultaneously map the heart while measuring voltages therein. The 3D geometric model is generated using data obtained by one or more electrodes on the catheters. While 3D geometric models allow viewing cardiac surfaces and various diagnostic maps at any angle by rotating them on a computer screen, the user does not see the whole cardiac surface at any time. In addition, in some situations the user cannot see the full picture of the catheter with respect to the cardiac surface geometry because there are background elements of the cardiac surface geometry that are obstructed by graphical elements of the cardiac surface geometry in the foreground.

In displaying 3D geometric models, such as 3D cardiac models of the heart, on a two-dimensional (2D) display, it is often difficult to see the entire diagnostic map (e.g. voltage map) at the same time. Thus, the 3D geometric model must be rotated in order to see different areas of the model. Furthermore, if the diagnostic map has animated graphics, the user may not be able to see the entirety of the graphics simultaneously because the animation will be running on the whole model (background and foreground) when the model is rotated. As the result, certain diagnostic map features and patterns might be difficult to identify using only a 3D geometric model of the heart.

Recent advancements in mapping technology have involved unfolding of 3D images into two-dimensional maps. For example, U.S. Pat. No. 7,542,595 to Moreau-Gobard describes unfolding of a 3D heart image using a ray-casting technique in order to more fully visualize coronaries and vessels on the surface of the heart. However, unfolding by such a technique produces significant distortion of the heart, rendering the resulting 2D image difficult to decipher.

BRIEF SUMMARY

The present disclosure is directed to systems and methods for projecting a 3D surface geometry onto a planar projection. In one embodiment, a method is for rendering a 2D planar representation from a 3D surface geometry of a chamber, the method comprising: obtaining a 3D surface geometry of a chamber; identifying a first surface section on the 3D surface geometry having a first feature of the chamber; selecting first and second points on the 3D surface geometry to form a cutting curve; and unfolding the 3D surface geometry at the cutting curve to render a 2D planar representation of the chamber; wherein the first and second points are selected to optimize representation of the first feature in the 2D planar representation.

In another embodiment, a method is for projecting a 3D surface geometry onto a planar projection, the method comprising: obtaining a 3D geometry of a chamber surface using an algorithm that generates angles and distances between points on the chamber surface that represent mapping information; applying a cutting curve to at least two points on the chamber surface; and at least partially unfolding at least a portion of the chamber surface along the cutting curve to form a planar projection that optimally preserves the angles and distances between points on the chamber surface.

In yet another embodiment, a method is for projecting a 3D surface geometry onto a planar projection, the method comprising: obtaining a 3D geometry of a chamber surface, the 3D geometry including mapping information, the mapping information comprising an area of interest and an area of disinterest; applying a cutting curve to at least two points on the chamber surface; and at least partially unfolding at least a portion of the chamber surface along the cutting curve to form a planar projection, wherein the planar projection minimizes distortion to the area of interest without regard to distortion of the area of disinterest.

BRIEF DESCRIPTION OF THE DRAWINGS

FIG. 9 is a view showing a planar projection of the heart chamber in FIG. 8, including the display of catheter electrodes and an interpolated voltage map.

DETAILED DESCRIPTION OF THE INVENTION

Figure 1:
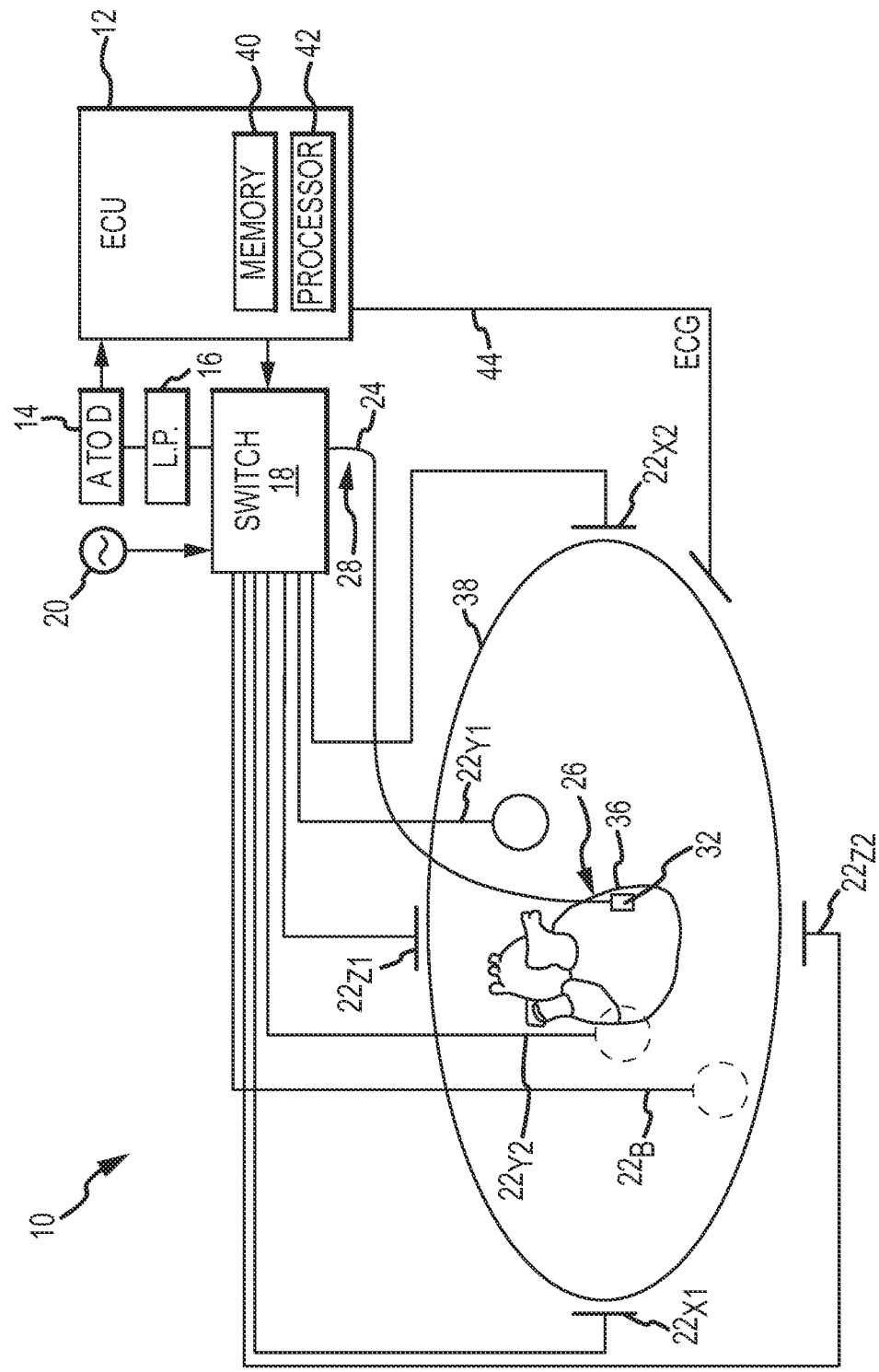
FIG. 1 is a diagrammatic depiction of an exemplary intracardiac mapping and navigation system.
Figure 2A:
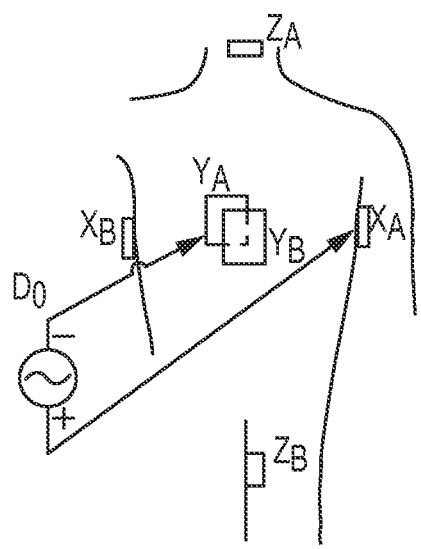
FIGS. 2A-2D are schematic diagrams of exemplary dipole pairs of driven body patch electrodes suitable for use with the intracardiac mapping and navigation system of FIG. 1.
Figure 2B:
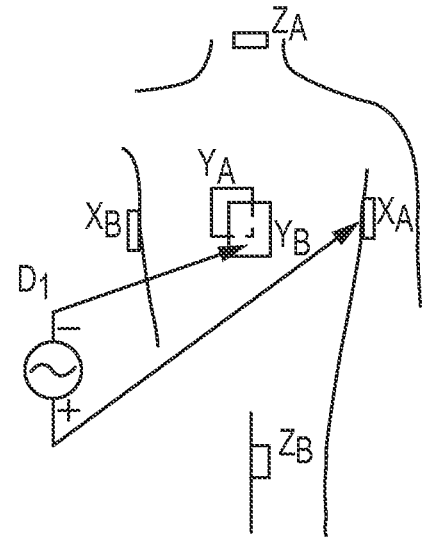
Figure 2C:
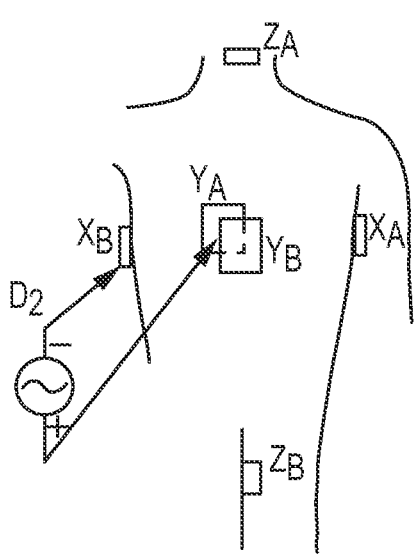
Figure 2D:
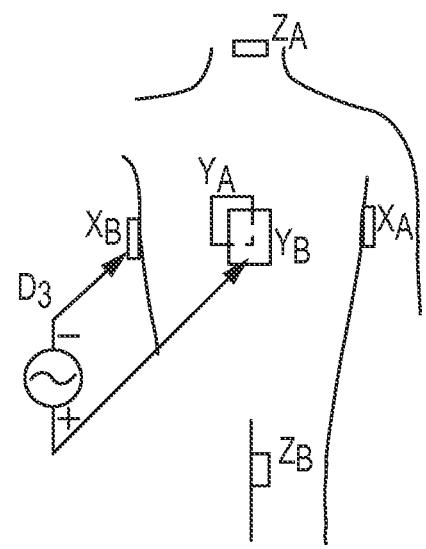

FIG. 1 is a diagrammatic depiction of an embodiment of exemplary mapping and navigation system 10. With reference to FIGS. 1-9, like numerals indicate the same or similar elements in the various views. System 10 may include various visualization, mapping and navigation components as known in the art, including, for example, an EnSite™ Velocity™ system commercially available from St. Jude Medical, Inc., or as seen generally, for example, by reference to U.S. Pat. No. 7,263,397, or U.S. Publication No. 2007/0060833, both of which are hereby incorporated by reference in their entireties as though fully set forth herein. With reference to the present disclosure, system 10 is configured to, among other things, collect cardiologic data, particularly electrocardiogram information, for a three-dimensional (3D) model of a heart, and to display such data in a user-friendly, two-dimensional (2D) format. Presenting 3D electrocardiogram information in an easy to understand 2D format facilitates identification of potential areas of interest for performing medical procedures, making diagnoses and the like. For example, users of system 10, such as clinicians, doctors, or cardiologists, may be able to more readily identify an ablation target for remedying a cardiac arrhythmia.

System 10 may include an electronic control unit (ECU) 12, analog-to-digital converter (A-to-D) 14, low-pass filter (L.P.) 16, switch 18, signal generator 20, and a plurality of body surface patch electrodes 22. System 10 may be electronically and/or mechanically coupled with an elongate medical device, such as, in one embodiment, a contact or non-contact mapping catheter (e.g., cardiac mapping catheter 24). Catheter 24 includes distal end portion 26 and proximal end portion 28. Distal end portion 26 includes electrode 32 and extends into heart 36 of patient 38. Proximal end portion 28 connects catheter 24 to switch 18.

System 10 may be configured to provide, among other things, mapping of patient tissue, such as one or more chambers of heart 36 of patient 38, and a 3D model bearing the surface geometry of the mapped tissue. Accordingly, ECU 12 may be configured to receive electrical measurements from one or more electrodes (diagrammatically shown as a single electrode 32 in FIG. 1) on mapping catheter 24 and, based on those measurements, to assess one or more electrical characteristics of tissue surrounding the distal end of mapping catheter 24. In an embodiment, ECU 12 may be configured to determine a voltage distribution of an endocardial surface according to electrical measurements from mapping catheter electrode 32. ECU 12 may be further configured to determine that voltage distribution with respect to an anatomical model, such as a model of one or more chambers, features, and/or surfaces of heart 36.

ECU 12 may include non-volatile memory 40 and processor 42 configured to perform many of the functions and operations described herein—i.e., memory 40 may store instructions for performing portions of one or more methods or processes described herein, and processor 42 may be configured to execute those instructions to perform the methods or processes. Memory 40 may also be configured to store an anatomical model, such as a cardiac chamber model, a plurality of measurements from mapping catheter 24, a plurality of terms and values for the methods described below, and other data and information. In an embodiment, ECU 12 may additionally or alternatively comprise a field-programmable gate array (FPGA) and/or other known computing device. In some embodiments, and as discussed further below, ECU 12 may be configured to perform a method of computing a 2D projection and/or a partially unfolded surface of a 3D model in order to better facilitate visualization of the model and features of the model.

In addition to (and as a part of) electrophysiology mapping, system 10 may be configured to determine the position and orientation (P&O) of mapping catheter 24 (e.g., of distal end portion 26) within patient 38. Accordingly, ECU 12 may be configured to control generation of one or more electrical fields and determine the position of one or more electrodes (e.g., electrode 32) within those fields. ECU 12 may thus be configured to control signal generator 20 in accordance with predetermined strategies to selectively energize various pairs (dipoles) of body surface patch electrodes 22, as described in greater detail below. In operation, ECU 12 may (1) obtain raw patch data (i.e., voltage readings) via filter 16 and A-to-D converter 14 and (2) use the raw patch data (in conjunction with electrode measurements) to determine the raw, uncompensated, electrode location coordinates of electrode 32 positioned inside heart 36 or a chamber thereof in three-dimensional space. ECU 12 may be further configured to perform one or more compensation and adjustment functions, and to output a location of electrode 32. Motion compensation may include, for example, compensation for respiration-induced patient body movement, as described in U.S. Publication No. 2012/0172702, which is hereby incorporated by reference in its entirety for all purposes.

Body surface patch electrodes 22 may be used to generate axes-specific electric fields within patient 38, and more specifically within heart 36. Three sets of patch electrodes may be provided: (1) electrodes 22X1, 22X2, (X-axis); (2) electrodes 22Y1, 22Y2, (Y-axis); and (3) electrodes 22Z1, 22Z2, (Z-axis). Additionally, a body surface electrode ("belly patch") 22B, may be provided as an electrical reference. Other surface electrode configurations and combinations are suitable for use with the present disclosure, including fewer electrodes 22, more electrodes 22, or different physical arrangements, e.g. a linear arrangement instead of an orthogonal arrangement.

Each patch electrode 22 may be independently coupled to switch 18, and pairs of patch electrodes 22 may be selected by software running on ECU 12 to couple patch electrodes 22 to signal generator 20. A pair of electrodes, for example the Z-axis electrodes 22Z1, 22Z2, may be excited by signal generator 20 to generate an electrical field in patient 38 and, more particularly, within heart 36. In one embodiment, this electrode excitation process occurs rapidly and sequentially as different sets of patch electrodes 22 are selected and one or more of the unexcited surface electrodes 22 are used to measure voltages. During the delivery of the excitation signal (e.g., current pulse), the remaining (unexcited) patch electrodes 22 may be referenced to belly patch 22B and the voltages impressed on these remaining electrodes 22 may be measured. In this fashion, patch electrodes 22 may be divided into driven and non-driven electrode sets. Low pass filter 16 may process the voltage measurements. The filtered voltage measurements may be transformed to digital data by analog to digital converter 14 and transmitted to ECU 12 for storage (e.g. in memory 40) under the direction of software. This collection of voltage measurements may be referred to herein as the "patch data." The software may have access to each individual voltage measurement made at each surface electrode 22 during each excitation of each pair of surface electrodes 22.

The patch data may be used, along with measurements made at electrode 32, to determine a relative location of electrode 32. The patch data may also be used along with measurements made at electrode 32 and/or other electrodes on catheter 24, such as a tip electrode, or on another device to determine a relative location of electrode 32 and/or the other electrodes. The discussion above and below describes determining the location of electrode 32, but it should be understood to apply to a tip electrode and other electrodes, as well. In some embodiments, potentials across each of the six orthogonal patch electrodes 22 may be acquired for all samples except when a particular surface electrode pair is driven. In embodiments, sampling a voltage with a particular patch electrode 22 while a surface electrode 22 acts as a source or sink in a driven pair may be avoided, as the potential measured at a driven electrode during this time may be skewed by the electrode impedance and the effects of high local current density. In an alternate embodiment, however, sampling may occur at all patch electrodes 22, even those being driven.

Generally, in an embodiment, three nominally orthogonal electric fields may be generated by a series of driven and sensed electric dipoles in order to determine the location of catheter 24 (i.e., of electrode 32). Alternately, these orthogonal fields can be decomposed and any pair of surface electrodes (e.g., non-orthogonal) may be driven as dipoles to provide effective electrode triangulation.

FIGS. 2A-2D show a plurality of exemplary non-orthogonal dipoles, designated D0, D1, D2 and D3. In FIGS. 2A-2D, the X-axis surface electrodes are designated XA and XB, the Y-axis surface electrodes are designated YA and YB, and the Z-axis electrodes are designated ZA and ZB. For any desired axis, the potentials measured across an intra-cardiac electrode 32 resulting from a predetermined set of drive (source-sink) configurations may be combined algebraically to yield the same effective potential as would be obtained by simply driving a uniform current along the orthogonal axes. Any two of patch electrodes 22 may be selected as a dipole source and drain, as noted above, with respect to a ground reference, e.g., belly patch 22B, while the unexcited body patch electrodes 22 measure voltage with respect to the ground reference. Electrode 32 placed in heart 36 is also exposed to the field from a current pulse, and voltages on electrode 32 are individually and separately measured with respect to ground, e.g., belly patch 22B.

Referring again to FIG. 1, data sets from each of patch electrodes 22 and electrode 32 are all used to determine the location of electrode 32 within heart 36. After the voltage measurements are made for a particular set of driven patch electrodes 22, a different pair of patch electrodes 22 may be excited by signal generator 20 and the voltage measurement process of the remaining patch electrodes 22 and electrode 32 takes place. The sequence may occur rapidly, e.g., on the order of one hundred times per second in an embodiment. To a first approximation the voltage on electrode 32 within heart 36 bears a linear relationship with position between patch electrodes 22 that establish the field within heart 36, as more fully described in U.S. Pat. No. 7,263,397 referred to above.

Some or all of the conventional twelve (12) ECG leads, coupled to additional body patches and designated collectively by reference numeral 44, may be provided to support the acquisition of an electrocardiogram (ECG) of the patient. As shown, ECG leads 44 may be coupled directly to the ECU 12 for acquisition and subsequent processing to obtain the phase of the heart in the cardiac cycle. Cardiac phase information may be used, in an embodiment, in mapping of electrical activity of heart 36, as described below.

In summary, FIG. 1 shows an exemplary system 10 that employs seven body patch electrodes 22, which may be used for injecting current and sensing resultant voltages. Current may be driven between two patches 22 at any time. Measurements may be performed between non-driven patch 22 and, for example, belly patch 22B as a ground reference. A patch bio-impedance, also referred to as a "patch impedance", may be computed according to the following equation:

$$BioZ[n \rightarrow m][k] = \frac{V_k}{I_{n \rightarrow m}}$$

where $V_k$ is the voltage measured on patch k and $I_{n \rightarrow m}$ is a known constant current driven between patches n and m. The position of electrode 32 may be determined by driving current between different sets of patches and measuring one or more patch impedances. In one embodiment, time division multiplexing may be used to drive and measure all quantities of interest. Position determining procedures are described in more detail in, for example, U.S. Pat. No. 7,263,397 and U.S. Publication No. 2007/0060833 referred to above. To perform an electrophysiology (e.g., mapping) procedure, distal end portion 26 of catheter 24 or multiple such catheters 24 may be manually guided to a desired location by a user such as a physician.

In addition to determining the positions of electrode 32, system 10 may also be configured to assess the electrical activity of the heart. Accordingly, ECU 12 may be further configured to perform one or more steps in one or more methods of determining a voltage distribution on a cardiac surface.

As briefly mentioned above, ECU 12 is configured to generate a three-dimensional (3D) surface geometry or 3D model of heart 36. The 3D model can be displayed as a planar image on a display connected to ECU 12. Furthermore, ECU 12 includes hardware and software for further processing the 3D model, such as for converting the 3D model into a two-dimensional (2D) projection or planar representation of the 3D model that can be displayed as a flat image in conjunction with, or alternatively to, the 3D model on the display. In some embodiments, the 2D projection can be used to determine features and patterns that would otherwise be difficult to visualize with only a 3D model.

Figure 3:
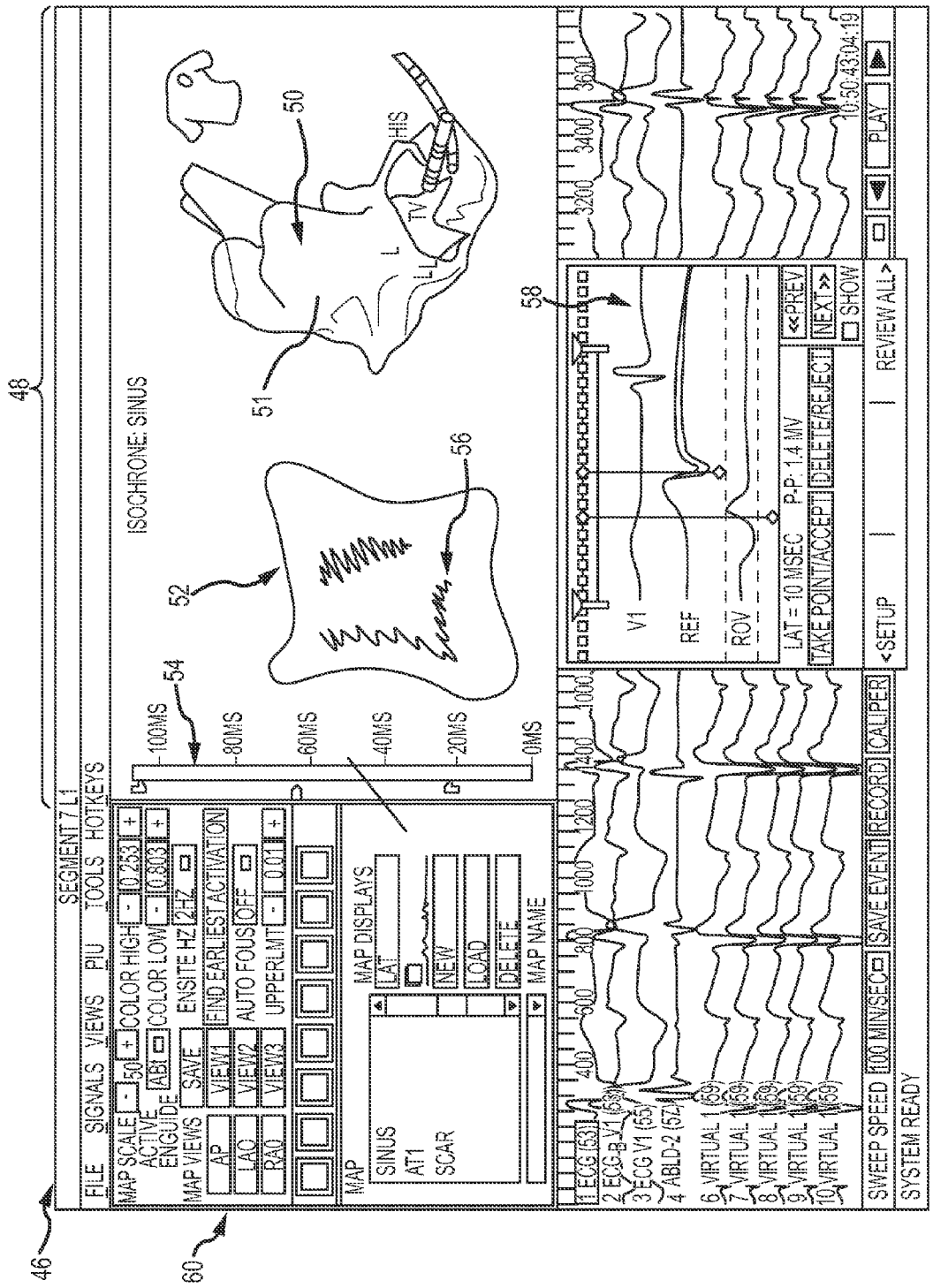
FIG. 3 is a display screen of the intracardiac mapping and navigation system of FIG. 1, showing a planar image of a three dimensional model of a heart.

FIG. 3 shows an exemplary computer display 46 that can be connected to ECU 12 of FIG. 1. Display 46 is used to show data to a physician or user of system 10, and to present certain options that allow the user to tailor system configuration for a particular use. It should be noted that the contents on the display can be easily modified and the specific data presented is illustrative and not limiting of the invention. Image panel 48 shows 3D model 50 of a heart chamber, which defines surface geometry 51. Surface geometry 51 of 3D model 50 is simultaneously displayed as 2D projection 52 in image panel 48. However, either of 3D model 50 or 2D projection 52 may be displayed individually. In FIG. 3, 3D model 50 is shown as a left atrium, but may comprise any heart chamber such as a ventricle. Additionally, system 10 may be used to map other chambers or hulls of patient 38 (FIG. 1) that can be displayed on image panel 48 as a 3D model.

3D model 50 includes "isochrones" in false color (shown in grayscale in FIG. 3) with guide bar 54, which are likewise shown as wave fronts 56 on 2D projection 52 in the same false color indicated by guide bar 54. In the image of FIG. 3, 3D model 50 has been generated using a catheter, such as catheter 24 (FIG. 1), to create a chamber representation that is displayed as a modeled hull shape (See FIG. 6). Display 46 also shows electrical activity of heart 36 (FIG. 1), such as the voltages associated with wave fronts 56. The electrical activity can also be shown as ECG information 58. The particulars of 3D model 50 (e.g. rotation, size, etc.), 2D projection 52 (e.g. cutting curve, orientation, etc.) and ECG information 58 (electrograms, QRS, etc.) can be specified and/or changed at user panel 60.

In an embodiment, one or more of the steps of the methods described below (e.g. with reference to FIGS. 4-7B) may be performed by ECU 12 (e.g., embodied in software stored in the memory 40 and executed by processor 42) to generate 3D model 50 and 2D projection 52. To address the issue of identifying features and patterns that might be useful in assessing, for example, ablation targets, an exemplary method includes, in addition to obtaining or generating the 3D model, the computation of a whole chamber map on a 2D planar image of a structure (e.g., the endocardial surface of a heart chamber) and/or an "unfolding" of the 3D chamber model that can be visualized all at once. Such maps could be useful, for example, as an aid in identifying certain global features and patterns of electrical excitations of the heart.

Figure 4:
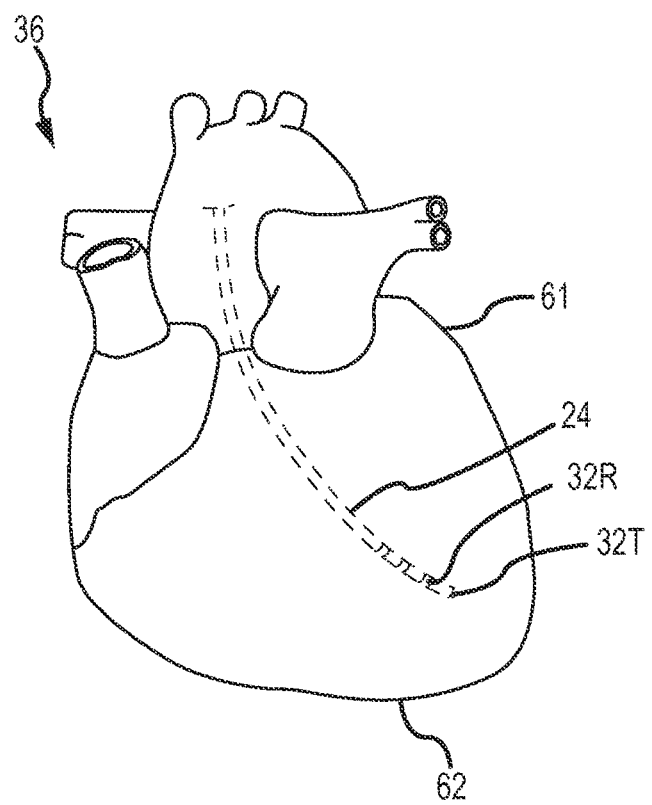
FIG. 4 is a perspective view of a heart schematically showing a catheter placed in a heart chamber.
Figure 5:
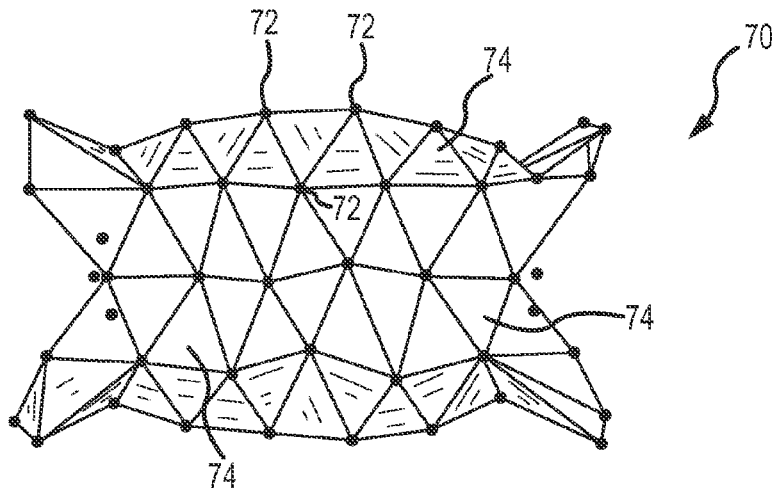
FIG. 5 is a schematic view of a modeled hull shape of the heart of FIG. 4
Figure 6:
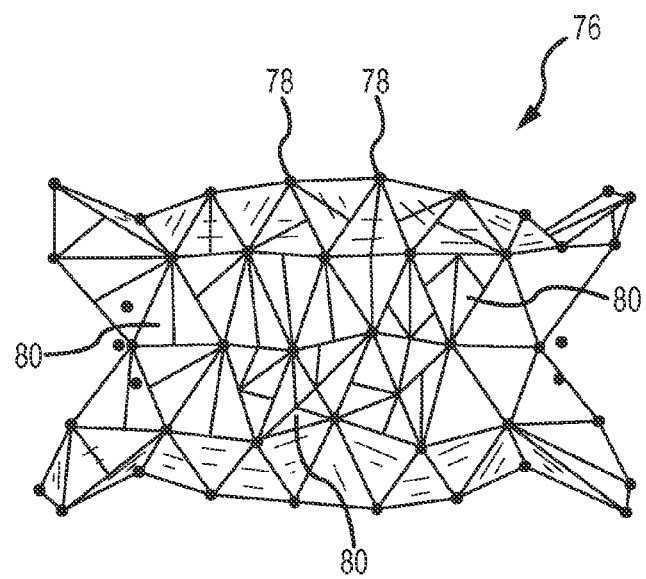
FIG. 6 is a schematic view of a re-meshed hull shape of the modeled hull shape of FIG. 5.
Figure 7A:
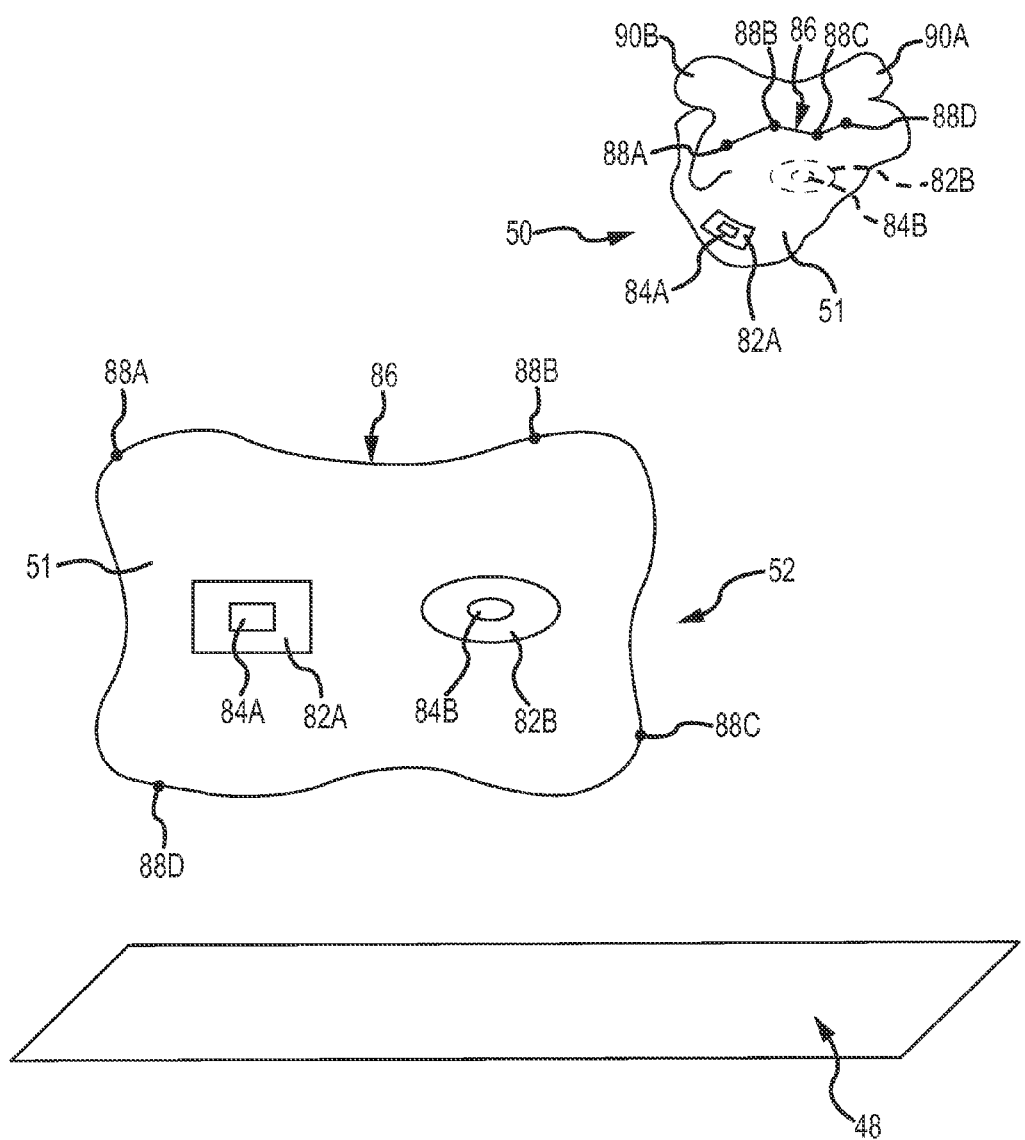
FIG. 7A is a schematic diagram showing the generation of a two-dimensional projection of a three-dimensional model of a heart for displaying as a planar image on a display panel.
Figure 7B:
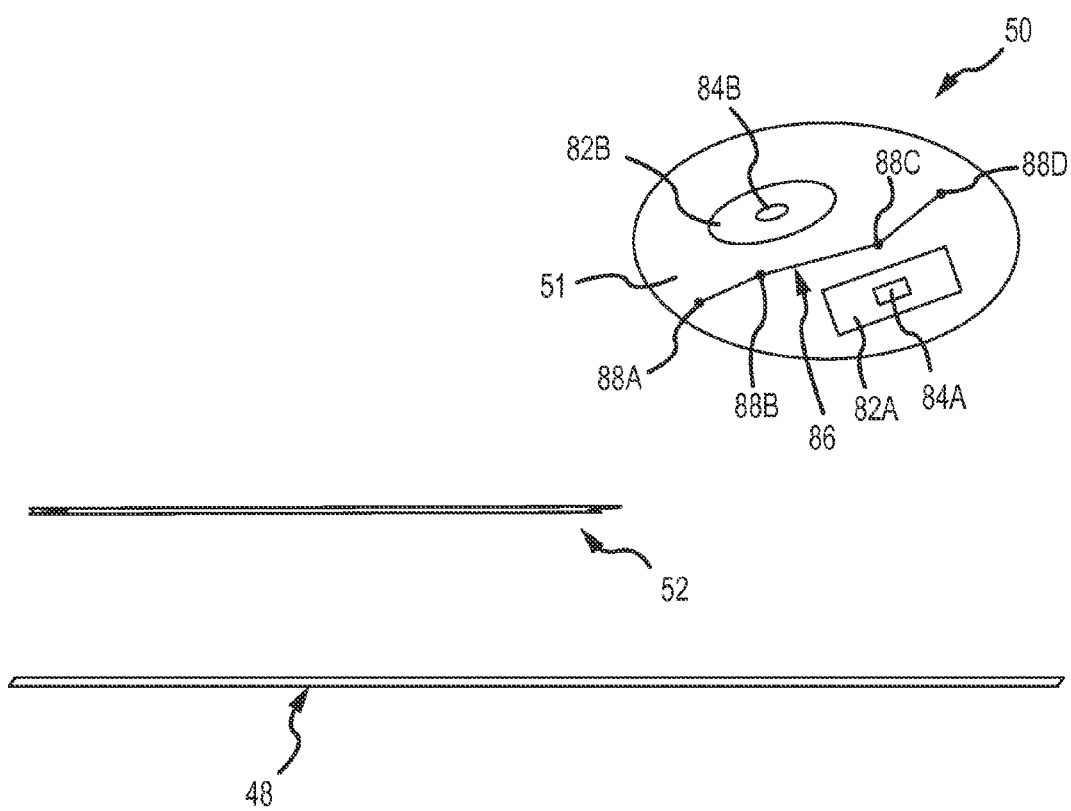
FIG. 7B is a schematic top view of the diagram of FIG. 7A showing the presentation of the two-dimensional projection and the three-dimensional model as planar images on a display panel.
Figure 8:
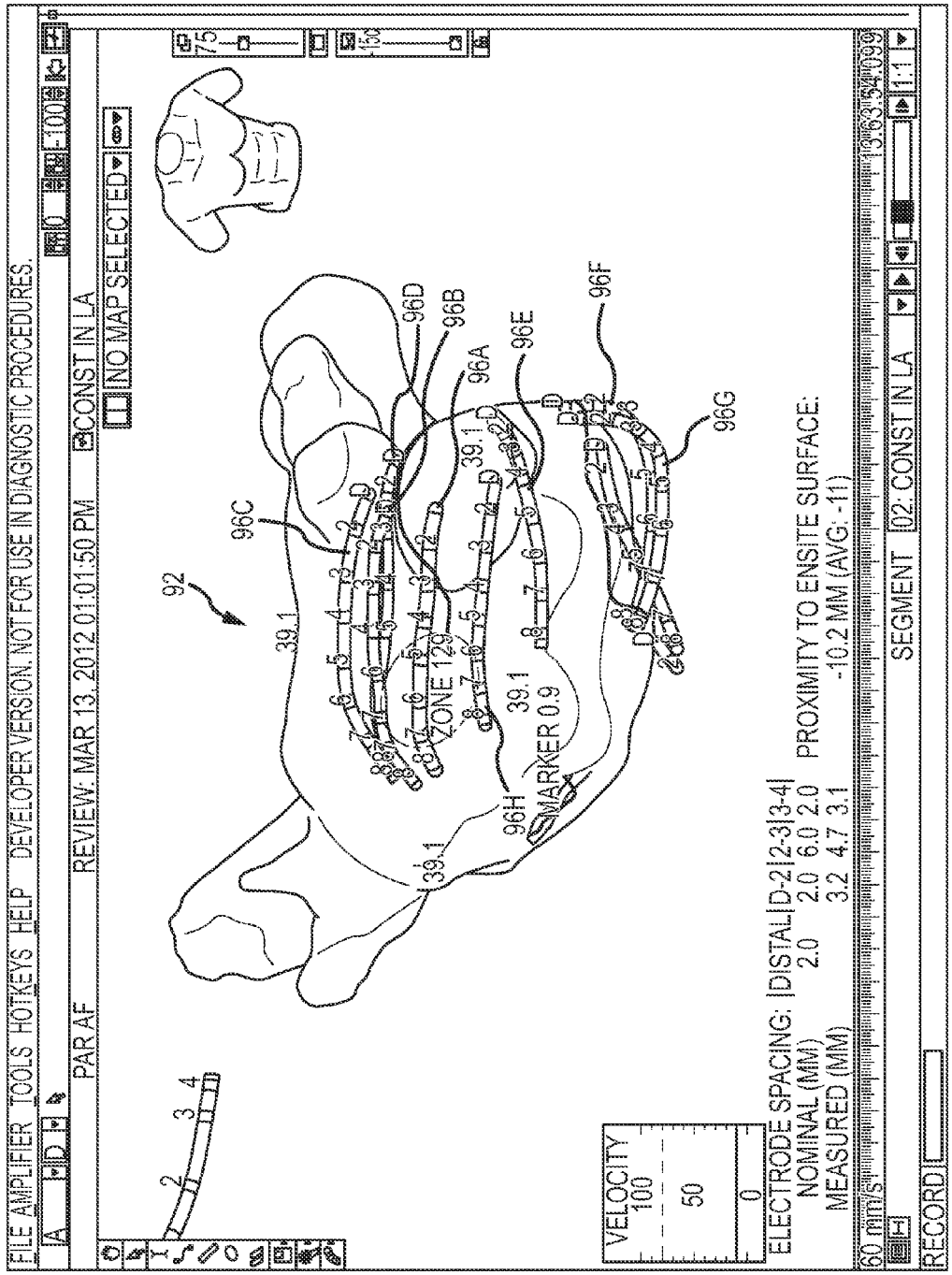
FIG. 8 is a view showing a three-dimensional drawing of a cardiac model of the left atrium of the heart as obtained, for example, with the system of FIG. 1.

FIGS. 4 and 5 illustrate the generation of a 3D model, such as 3D model 50, from heart 36. FIG. 6 illustrates a re-meshing of a 3D model from FIG. 5 that is used to generate a 2D projection, such as 2D projection 52. FIGS. 7A and 7B illustrate the generation of planar images of surface geometry 51 for 3D model 50 and 2D projection 52 of heart 36. FIGS. 8 and 9 show screen shots of a plurality of catheters inserted into a 3D model of a left atrium, and a 2D projection of the left atrium and the catheters, respectively.

Generally, a method of rendering a 2D planar representation from a 3D surface geometry of a chamber comprises generating 3D model 50, selecting points on surface geometry 51 of 3D model 50 to form a cutting curve, and unfolding surface geometry 51 at the cutting curve to render a 2D planar representation of the chamber. Thus, "unfolding" a 3D model conceptually comprises making an incision in the hollow hull that forms the 3D model and stretching the hull at the incision so that the edge of the incision forms the edge of a 2D projection or planar representation. As mentioned, the 3D model can be re-meshed to minimize distortion of the entire 2D planar representation. Furthermore, the cutting curve can be positioned on the 3D model to minimize distortion of particular features of interest on the surface geometry in the 2D planar representation. In an embodiment, the 3D model can be partially, instead of fully, unfolded to show only the particular features of interest.

FIG. 4 is a perspective view of heart 36 schematically showing catheter 24 placed inside of left atrium 61 and left ventricle 62. Catheter 24 may be a conventional EP catheter, as described above with reference to FIGS. 1 and 2. Catheter 24 includes electrodes, such as tip electrode 32T and ring electrode 32R. While electrodes 32T and 32R lie on a surface of a chamber within heart 36 and when signal generator 20 (FIG. 1) is "off", each electrode can be used to measure the voltage on the heart surface. The magnitude of this voltage as well as its timing relationship of the signal with respect to the heartbeat events are measured and presented to the user through display 46 (FIG. 3). The peak to peak voltage measured at a particular location on the heart wall shows areas of diminished conductivity and may reflect an infracted region of the heart. The timing relationship data are typically displayed as "isochrones" on display 46. In essence, regions that receive the depolarization waveform at the same time are shown in the same false color or gray scale. Since electrodes 32T and 32R lie within heart 36, the location process described above can be used to detect their location inside of left atrium 61 and/or left ventricle 62. The detected locations are collected as a set of points that is used to generate 3D model 50, which maps the surface geometry 51, or topological features, of heart 36.

FIG. 5 is a schematic view of modeled hull shape 70 of heart 36 of FIG. 4. Modeled hull shape 70 comprises points 72 and panels 74. Modeled hull shape 70 represents the cloud of points 72 collected from catheter 24 in FIG. 4 to form left atrium 61. Modeled hull shape 70 forms a hollow body that represents connections between the most exterior of points 72 in the data set. Usually the hull is composed of triangular panels 74 having a semi-regular form. Points 72 can be resampled to increase the number of points for further computation. The resampling process interpolates between vertices on the exterior of the polygon. In essence, intermediate points are defined within each facet of the hull or polyhedron as represented by a data point. Although the resampling process creates "fictitious" interpolated points within an enhanced data set, these points are useful in the modeling operation. Modeled hull shape 70 may comprise a completed model that can be shown on display 46 as 3D model 50. The method of FIG. 5 generally shows the generation of alpha shapes for modeling convex hulls, as is described in more detail in U.S. Pat. No. 8,253,725, which is incorporated herein by reference.

Other methods for gathering data points and generating curves that represent 3D model 50 can be used. For example, smooth curves can be fit to the enhanced set of data points generated by the resampling process. Conventional smoothing algorithms are used corresponding to a least squares fit. This process yields a mathematically differentiable surface that is easily visualized and manipulated. Such smoothing processes are described in greater detail in U.S. Pat. No. 7,263,397 referred to above. Other methods for generating 3D models include the use of convex hull shapes, as are known in the art. For any method of generating 3D model 50, a surface geometry is shown on display 46 that allows a user of system 10 to visualize chambers of heart 36, such as left atrium 61 and left ventricle 62.

In the present disclosure, the collection of data forming a 3D model, such as points 72 and panels 74 forming 3D model 50, can be further processed to generate a 2D projection. There are various ways in which a 2D projection could be computed. In some embodiments, a center of projection can be placed somewhere inside a surface of the 3D model using, for example, a variant of spherical coordinates. To obtain the planar representation of the chamber, one can drop the radius from the spherical coordinates and retain only the angles. In some embodiments, the planar projections could be supplemented by proper annotations (as discussed in greater detail below with reference to FIG. 9), which could include anatomical features and catheter electrodes in the proximity of the surface, among other things. In some embodiments, the diagnostic maps (e.g. electrocardiogram information) pertaining to the surface can be drawn on the planar projection or an unfolded 3D view of the chamber.

Recent advances in computational geometry and processing speed permit a more sophisticated cutaway view, unfolding a general surface model onto something more hemispherical but still recognizable as that chamber, and minimizing distortions of angle and area. In particular, 3D model 50 can be re-meshed into a collection of points and surfaces more readily transformed into a 2D image that minimizes distortion of the features of the 3D model in a flattened picture, enabling a user to make more meaningful interpretations of the data. The ability to visualize an unfolded view of the entire endocardial surface at once, without using a clipping plane as was previously needed, is desirable to, among other things, preserve the ability of a user of system 10 to interpret data on the 2D image.

FIG. 6 is a schematic view of re-meshed hull shape 76 of modeled hull shape 70 of FIG. 5. Re-meshed hull shape 76 includes points 78 and panels 80. Points 78 and panels 80 are laid out in a manner that is readily adapted to "unfolding" 3D model 50 into a 2D planar representation. Possible algorithms for generating re-meshed hull shape 76 and a resulting 2D planar representation include Least Squares Conformal Mapping (which has a Matlab toolbox). Additionally, the adaptive resampling re-meshing algorithm from Semechko, et al. ("High Quality Remeshing of Closed Genus-0 Surfaces," Medical Image Computing and Computer Assisted Intervention 2011, Toronto, Calif., 2011) and the parameterization re-meshing algorithm of Alliez, et al. ("Interactive Geometry Remeshing," ACM SIGGRAPH 21, 347-354, 2002), both of which are incorporated herein by reference in their entirety for all purposes, may be used improve the 2D projectability, or unfoldability, of a 3D hull. Re-meshed hull shape 76 optimally preserves angles, distances, areas and the like of 3D model 50 when unfolded as 2D projection 52. Optimally preserving 3D model 50 is a tradeoff between preserving angles and distances, and the embodiments described herein make appropriate tradeoffs to give a user of system 10 visually pleasing, accurate images that are useful in performing medical procedures and diagnostics. In one embodiment that uses a re-meshing algorithm, such as that of Alliez, et al., the re-meshed surfaces comprise equilateral or nearly equilateral triangles that increase the resolution of the 3D model without distorting the basic image represented when projected as a 2D planar representation.

FIG. 7A is a schematic diagram showing the generation of two-dimensional (2D) projection 52 of three-dimensional (3D) model 50, which represents left atrium 61 of heart 36 (FIG. 4). FIG. 7B is a schematic top view of the diagram of FIG. 7A showing the presentation of 2D projection 52 and 3D model 50 as planar images on image panel 48. FIGS. 7A and 7B are discussed concurrently.

3D model 50 and 2D projection 52 are viewable on image panel 48 of display 46 (FIG. 3) as planar images. 3D model 50 comprises a smoothed surface, such as modeled hull shape 70 of FIG. 5, having a particular surface geometry 51. In FIGS. 7A and 7B, 3D model 50 is shown without gridlines for clarity. 3D model 50 includes first surface section 82A and second surface section 82B, which include first feature 84A and second feature 84B, respectively. Cutting curve 86 extends along the surface of 3D model 50 and passes through points 88A, 88B, 88C and 88D.

3D model 50 represents the exterior surface hull of left atrium 61 of FIG. 4, for example. 3D model 50 includes a generally smooth lower portion and a curved upper portion. The lower smooth portion includes areas of interest to a user of system 10, such as a cardiologist. For example, first surface section 82A and second surface section 82B may include myocardium that has weak or malfunctioning electrical activity, with features 84A and 84B representing specific local electrical activity, such as rotors. The curved upper portion includes areas of high curvature, such as pulmonary veins 90A and 90B.

As is illustrated in FIGS. 7A and 7B, only one of surface sections 82A and 82B can be seen at a time on 3D model 50 from image panel 48. Thus, it becomes necessary for a user of system 10 to rotate 3D model 50 between two or more positions, such as by using user panel 60 on display 46 (FIG. 3), to see the complete electrical pattern between sections 82A and 82B. In order to more readily visualize surface sections 82A and 82B, 3D model 50 is unfolded into 2D projection 52 (not drawn to scale in FIGS. 7A and 7B) so that surface sections 82A and 82B can be simultaneously viewed on image panel 48. In particular, 2D projection 52 can comprise a complete unfolding of surface geometry 51 such that the entirety of 3D model 50 is shown. In other embodiments, 2D projection 52 can comprise a partial unfolding of 3D model 50 such that only sections 82A and 82B are shown and areas related to veins 90A and 90B are omitted.

In order to unfold 3D model 50, the collection of data points representing the model are re-meshed into a higher resolution collection of data points. For example, the data representing points 72 and panels 74 (FIG. 5) is converted into data representing points 78 and panels 80 (FIG. 6). In one embodiment, re-meshed hull shape 76 may be displayed as 3D model 50. Next, cutting curve 86 is positioned on surface geometry 51 to initiate the "unfolding." Cutting curve 86 can be positioned anywhere on surface geometry 51. However, the position of cutting curve 86 can be selected to minimize distortion to sections 82A and 82B. To that end, cutting curve 86 can be positioned away from sections 82A, near areas where distortion is tolerable in the 2D planar representation. Furthermore, the distortion of sections 82A and 82B can be minimized by placing cutting curve 86 near an area of surface geometry that will inherently result in distortion, such as an area of high curvature like veins 90A and 90B. Additionally, distortion of sections 82A and 82B can be minimized by sizing the total length of cutting curve 86 to be greater than the dimensions of sections 82A and 82B. Furthermore, cutting curve 86 can include multiple points and segments in order to better position cutting curve 86 on surface geometry 51. For example, rather than have cutting curve 86 extend linearly between points 88A and 88D, intermediary points 88B and 88C can be added to guide cutting curve 86 along a desired route on surface geometry 51. Although, in some embodiments, cutting curve 86 may comprise a straight line. In yet other embodiments, cutting curve 86 may comprise a closed curve, wherein ends of the curve meet to form an area that is removed from the 3D model before being stretched into the 2D planar representation.

System 10 can be configured to automatically select the shape and position of cutting curve 86 to minimize distortion. A user of system 10 may specify areas of interest and areas of disinterest on 3D model 50. For example, sections 82A and 82B can be highlighted or identified on 3D model 50 as being areas of interest, while pulmonary veins 90A and 90B can be highlighted or identified as being areas of disinterest. In one embodiment, a user of system 10 may draw on image panel 48 of display 46 (FIG. 3) to identify various areas of 3D model 50. Based on these inputs, ECU 12 (FIG. 1) can place cutting curve 86 on surface geometry to maximize preservation of features 84A and 84B upon unfolding. For example, the placement, overall length and the number of segments of cutting curve 86 can be automatically determined by system 10. Alternatively, cutting curve 86 can be manually drawn on 3D model 50 at image panel 48.

System 10 can also be configured to automatically regenerate 2D projection 52 at appropriate times. For example, a user of system 10 may determine that a different area of interest on 3D model 50 is to be viewed and analyzed for a different procedure or purpose. Thus, surface sections 82A and 82B may no longer be areas of interest and it is no longer desirable to minimize the distortion of 2D projection 52 at surface sections 82A and 82B. The user may rotate 3D model 50 as shown in display panel 48 such that a different 2D planar image is shown and a different area of interest can be highlighted. ECU 12 can thus recalculate the parameters for cutting curve 86 in order to minimize the distortion to the newly selected area of interest in the 2D planar representation of image panel 48.

Once 3D model 50 has been unfolded into 2D projection 52, image panel 48 can be augmented with various features to facilitate mapping, diagnosis, treatment and the like, as discussed with reference to FIGS. 8 and 9.

FIG. 8 is a view showing a three dimensional drawing of cardiac model 92 of a left atrium, as obtained with an intracardial navigational system, such as system 10 of FIG. 1. FIG. 9 is a view showing planar projection 94 of the heart chamber in FIG. 8. FIG. 8 shows catheters 96A-96H, each having a group of electrodes that are shown in FIG. 9 as dots.

FIG. 9 also shows an interpolated voltage map, which may be obtained with catheters 96A-96H, superimposed over planar projection 94. The voltage map depicts wave fronts of the electrical excitation, which could be useful in the visual identification of potential atrial fibrillation (AF) drivers such as rotors, foci, etc. In some embodiments, the magnitude of the voltages can be displayed as different colors (e.g., different pixel colors) on image panel 48. Color-coding for the interpolated voltages is shown on guide bar 98. In some embodiments, the interpolated voltage between the electrodes can be computed using a Thin Plate Splines method. Other techniques for interpreting the voltages can also be employed.

FIG. 8 shows catheters 96A-96H arranged generally horizontally (with reference to the orientation of FIG. 8) so that the electrodes are arranged three-dimensionally in a cylindrical pattern against the interior walls of the left atrium. As such, it may be difficult to discern which electrodes are in the foreground and which are in the background. FIG. 9 shows the electrodes for catheters 96A-96H unfolded into a two-dimensional planar pattern. Thus, the entire electrical activity of the left atrium in conjunction with the location of all of the electrodes can be clearly seen in one view.

In addition to identifying each of the electrodes with an identifier and showing guide bar 98, the image displayed on image panel 48 along with the 2D planar projection can include other annotations that, among other things, provide a viewer of image panel 48 with orientation of the heart chamber. For example, the names of features of cardiac model 92 can be shown, such as left lateral wall, septum, mitral valve, etc. Tape measures and/or grid coordinates on the planar or partially unfolded surfaces can also be used to show the corresponding distance values from the original surface. Additionally, diagnostic information may be recorded on the 2D planar projection and recorded for later viewing.

In some embodiments, a planar map (e.g. a 2D model such as that shown in FIG. 9, FIG. 3, or FIGS. 7A and 7B having superimposed diagnostic/electrical data) can be used to detect one or more potential ablation sites and/or to visually confirm the results of various diagnostic algorithms pointing to potential ablation target sites. The 2D planar projection provides a simultaneous view of the heart geometry along with the associated electrical activity while preserving, as best as possible, the angles and distances between points on the surface. As such, complete performance of the heart chamber is intuitively presented.

The 2D planar projection can be used to render any of a number of different types of diagnostic maps on the planar projections or partially unfolded surfaces. Animated planar maps can also be generated and shown in real-time to aid in the diagnosis and treatment of arrhythmias. For example, real-time electrical activity can be superimposed on the 2D planar projection. As discussed above, in some embodiments, a 3D model can be rotated or tilted to allow a better view of a particular area on the surface geometry. In order to facilitate real-time viewing and regeneration of the 2D planar projection, ECU 12 can be configured to provide indicator 100 that gives a user of system 10 a level of feedback regarding the distortion level of the presented 2D planar projection. Indicator 100 may comprise any suitable indicator, such as a dial, an analogue indicator or a digital indicator. The distortion level may be determined, for example, by comparing a data set from the 2D planar projection to a data set from the original 3D model or a data set from a reference or idealized 2D planar projection. In other embodiments, an indicator can be provided directly on the surface of the 2D planar projection itself. For example, a square or triangle grid could be provided on the 2D planar projection to indicate areas of distortion. In another embodiment, the transparency of the 2D planar projection could be varied to indicate different levels of distortion, e.g., areas of high distortion could be highly transparent with areas of low distortion being more opaque.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by referenced herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

What is claimed is:

1. A method of rendering a 2D planar representation from a 3D surface geometry of a chamber, the method comprising:
   obtaining a 3D surface geometry of the chamber;
   identifying a first surface section on the 3D surface geometry having a first feature of the chamber;
   selecting first and second points on the 3D surface geometry to form a cutting curve; and
   unfolding the 3D surface geometry at the cutting curve to render a 2D planar representation of the chamber;
   wherein the first and second points are selected to facilitate representation of the first feature in the 2D planar representation; and
   displaying the 2D planar representation as a planar image on a display unit; and
   wherein the first and second points are positioned on the 3D surface geometry to minimize distortion of the first feature after unfolding and the cutting curve is positioned away from the first surface section.

2. The method of claim 1, wherein the first and second points are positioned on the 3D surface geometry to selectively ignore distortion to portions of the chamber after unfolding.

3. The method of claim 2, wherein the cutting curve is positioned in proximity to areas of high curvature of the 3D surface geometry.

4. The method of claim 1, wherein the cutting curve has a length greater than that of the first surface section.

5. The method of claim 1, wherein a plurality of cutting curves are formed to unfold the 3D surface geometry.

6. The method of claim 1, wherein the first and second points are automatically selected to determine the cutting curve that minimizes distortion of the first feature.

7. The method of claim 1, wherein the 3D surface geometry is re-meshed such that rendering of the 2D planar representation preserves angles and distances of the 3D surface geometry after unfolding.

8. The method of claim 1, further comprising generating a conformal map from the 3D surface geometry, wherein the first and second points are selected on the conformal map.

9. The method of claim 8, further comprising adaptively resampling the conformal map before selecting the first and second points.

10. The method of claim 1, further comprising simultaneously displaying the 3D surface geometry with the 2D planar representation in the planar image.

11. The method of claim 1, further comprising:
    adjusting an orientation of the 3D surface geometry in space;
    identifying a second surface section having a second feature of the chamber on the 3D surface geometry;
    forming a new cutting curve that will preserve representation of the second feature after unfolding;
    unfolding the 3D surface geometry at the new cutting curve to render a new 2D planar image; and
    displaying the second surface section and the second feature as the planar image.

12. The method of claim 1, wherein the 2D planar representation is annotated in the planar image with a name of the first feature.

13. The method of claim 1, further comprising providing feedback on the planar image of a distortion level of the first surface section between the 2D planar representation and the 3D surface geometry.

14. The method of claim 1, wherein:
    the chamber is an atrium or ventricle of a heart; and
    further comprising displaying voltages of the heart on the planar image.

15. The method of claim 1, further comprising:
    identifying a second surface section having a second feature of the chamber on the 3D surface geometry, the second surface section being located on a portion of the 3D surface geometry with an obstructed view of the first surface section;
    selecting the first and second points to preserve representation of the first and second features; and
    unfolding the 3D surface geometry to simultaneously view the first surface section and the second surface section.

16. A method for projecting a 3D surface geometry onto a planar projection, the method comprising:
    obtaining a 3D geometry of a chamber surface using an algorithm that generates angles and distances between points on the chamber surface that represent mapping information;
    applying a cutting curve to at least two points on the chamber surface, the cutting curve positioned in proximity to areas of high curvature on the 3D surface geometry;
    at least partially unfolding at least a portion of the chamber surface along the cutting curve to form a planar projection that preserves the angles and distances between points on the chamber surface; and
    wherein the at least two points are positioned on the 3D surface geometry to selectively ignore distortion to portions of the chamber surface after folding.

17. The method of claim 16, further comprising re-meshing the 3D geometry into a uniform or regularized mesh.

18. The method of claim 17, further comprising generating a conformal map from the 3D geometry before applying the cutting curve.

19. The method of claim 18, wherein the cutting curve is selected to minimize distortion to the planar projection by positioning the cutting curve near areas of the 3D geometry where distortion is tolerable.

20. The method of claim 16, wherein the at least two points are positioned on the 3D geometry to minimize distortion of an area of interest of the mapping information after unfolding.

21. The method of claim 20, further comprising:
    re-forming the cutting curve to preserve representation of a new area of interest after unfolding; and
    unfolding the chamber surface along the new cutting curve to form a new planar projection.

22. The method of claim 16, wherein a plurality of cutting curves are selected to unfold the 3D geometry.

23. The method of claim 16, wherein the cutting curve is automatically selected to determine the cutting curve that minimizes distortion of the mapping information.

24. The method of claim 16, wherein the planar projection is annotated with descriptors of mapping information.

25. The method of claim 16, further comprising providing feedback of a distortion level of the mapping information between the planar projection and the 3D geometry.

26. The method of claim 16, wherein the chamber surface is an atrium or ventricle of a heart.

27. The method of claim 26, further comprising displaying voltages of the heart on the planar projection.

28. The method of claim 16, further comprising:
identifying first and second features on the chamber surface;
positioning the cutting curve to preserve representation of the first and second features; and
at least partially unfolding at least a portion of the chamber surface along the cutting curve to form a planar projection that simultaneously shows the first and second features.

29. The method of claim 16, further comprising simultaneously displaying the 3D geometry and the planar representation of the chamber surface in an output image.

30. A method for projecting a 3D surface geometry onto a planar projection, the method comprising:
obtaining a 3D geometry of a chamber surface, the 3D geometry including mapping information, the mapping information comprising:
an area of interest; and
an area of disinterest;
generating a conformal map from the 3D geometry;
adaptively resampling the conformal map;
selecting at least two points from the conformal map; and
applying a cutting curve to the at least two points on the chamber surface; and
at least partially unfolding at least a portion of the chamber surface along the cutting curve to form a planar projection, wherein the planar projection minimizes distortion to the area of interest without regard to distortion of the area of disinterest.

* * * * *